United States Patent
El Menyawi et al.

(10) Patent No.: US 10,144,774 B2
(45) Date of Patent: Dec. 4, 2018

(54) METHOD FOR PURIFYING IGG

(71) Applicant: CSL Behring AG, Bern (CH)

(72) Inventors: Ibrahim El Menyawi, Bern (CH); Doreen Siegemund, Aarwangen (CH)

(73) Assignee: CSL BEHRING AG, Bern (CH)

( * ) Notice: Subject to any disclaimer, the term of this patent is extended or adjusted under 35 U.S.C. 154(b) by 326 days.

(21) Appl. No.: 14/900,499

(22) PCT Filed: Jul. 1, 2014

(86) PCT No.: PCT/EP2014/063939
§ 371 (c)(1),
(2) Date: Dec. 21, 2015

(87) PCT Pub. No.: WO2015/000886
PCT Pub. Date: Jan. 8, 2015

(65) Prior Publication Data
US 2016/0368970 A1 Dec. 22, 2016

(30) Foreign Application Priority Data
Jul. 1, 2013 (EP) .................................. 13175421

(51) Int. Cl.
*C07K 1/30* (2006.01)
*C07K 16/06* (2006.01)
*B01D 15/36* (2006.01)

(52) U.S. Cl.
CPC .......... *C07K 16/065* (2013.01); *B01D 15/363* (2013.01); *C07K 1/30* (2013.01); *C07K 2317/14* (2013.01)

(58) Field of Classification Search
None
See application file for complete search history.

(56) References Cited

U.S. PATENT DOCUMENTS

| | | | |
|---|---|---|---|
| 5,164,487 A | 11/1992 | Kothe et al. | |
| 5,886,154 A | 3/1999 | Lebing et al. | |
| 9,828,418 B2 * | 11/2017 | El Menyawi | C07K 16/00 |
| 2006/0142549 A1 * | 6/2006 | Takeda | C07K 1/30 |
| | | | 530/351 |

FOREIGN PATENT DOCUMENTS

| | | | |
|---|---|---|---|
| EP | 0 893 450 A1 | 1/1999 | |
| EP | 1 561 756 A1 | 8/2005 | |
| WO | WO 99/64482 | 12/1999 | |
| WO | WO-2005073252 A1 * | 8/2005 | ............ A61L 2/0011 |

OTHER PUBLICATIONS

Bertolini "Production of plasma proteins for therapeutic use" Wiley books, section 4 "The pharmaceutical environment applied to plasma fractionation" pp. 383-448 (Year: 2012).*
Chanutin and Curnish., "The Precipitation of Plasma Proteins by Short-Chain Fatty Acids," (1960) Arch. Biochem. Biophys, 89; 218-220.
Cohn, et al., "Preparation and Properties of Serum and Plasma Proteins. IV. A System for the Separation into Fractions of the Protein and Lipoprotein Components of Biological Tissues and Fluids," (1946), J Am Chem Soc, 68, 459-475.
Extended European Search Report of European Application No. 13174521.8 dated Sep. 13, 2013 (5 pages).
Habeeb and Francis,"Preparation of Human Immunoglobulin by Caprylic Acid Preparation," (1984) Prep. Biochem. 14(1), 1-17.
International Search Report and the Written Opinion of the International Searching Authority for International Application No. PCT/EP2014/063939, dated Aug. 27, 2014 (8 pages).
Kistler and Nitschmann, "Large Scale Production of Human Plasma Fractions," (1962), Vox Sang, 7, 414-424.
Oncley et al., "The Separation of the Antibodies, Isoagglutinins, Prothrombin, Plasminogen and $\beta_1$-Lipoprotein into Subtractions of Human Plasma," (1949), J Am Chem Soc, 71, 541-550.
Steinbuch and Audran, "The Isolation of IgG from Mammalian Sera with the Aid of Caprylic Acid," (1969) Arch. Biochem. Biophys. 134, 279-284.
Steinbuch et al., "Preparation of an IgM and IgA Enriched Fraction for Clinical Use," (1973), Prep. Biochem 3, 363-373.

* cited by examiner

*Primary Examiner* — Daniel E Kolker
*Assistant Examiner* — James L Rogers
(74) *Attorney, Agent, or Firm* — Finnegan, Henderson, Farabow, Garrett & Dunner, L.L.P.

(57) ABSTRACT

The invention relates to a modified process for the purification of IgG, improving the yield of IgG per liter of starting material without compromising the quality of the product.

21 Claims, 3 Drawing Sheets

(a)

(b)

(c)

METHOD FOR PURIFYING IGG

Figure 1:
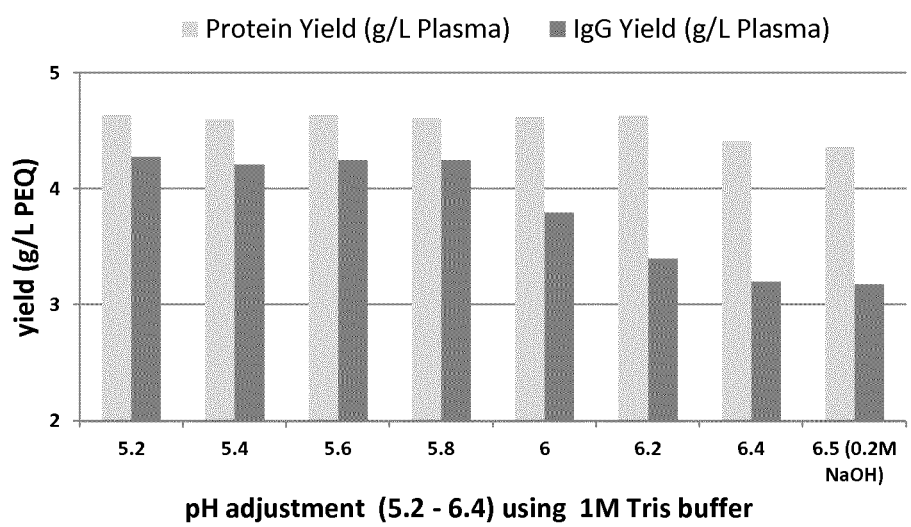

This application is the national stage entry under 35 U.S.C. § 371 of International Application No. PCT/EP2014/063939, filed on Jul. 1, 2014, which claims priority to European Application No. 13174521.8, filed Jul. 1, 2013. The contents of these applications are each incorporated herein by reference in their entirety.

The invention relates to an improved process for the purification of IgG. In particular, the improved process provides higher yields than previous processes.

BACKGROUND TO THE INVENTION

As is well known, immunoglobulins play an important role in the immune system of mammals. They are produced by B-lymphocytes, found in blood plasma, lymph and other body secretions. Immunoglobulins constitute approximately 20% of the plasma proteins in humans. The basic unit of immunoglobulins is a heterotetramer, containing 2 heavy chains and two light chains, linked by disulphide bonds. Each of these chains have a variable region at their N-terminus which form the antigen binding site, and constant regions, which are responsible for the effector functions of the immunoglobulins.

There are five major classes of immunoglobulins with differing biochemical and physiological properties: IgG ($\gamma$ heavy chain), IgA ($\alpha$), IgM ($\mu$), IgD ($\delta$) and IgE ($\epsilon$). Human IgG represents the most abundant immunoglobulin in plasma, whereas IgA represents the main antibody class in external secretions such as saliva, tears and mucus of the respiratory and intestinal tracts. IgM is by far the physically largest antibody in the human circulatory system, usually being present as a pentamer of the basic immunoglobulin unit, and appears early in the course of an infection.

Initially, IgG preparations from human plasma were successfully used for the prophylaxis and treatment of various infectious diseases. The early products were produced by relatively crude processes (ethanol fractionation), and contained impurities and aggregates to an extent that they could only be administered intramuscularly. Improvements in the purification processes have led to IgG preparations that were suitable for intravenous administration (called IVIG) due to their improved purity and quality, and preparations for subcutaneous administration (called SCIG) have also been developed.

The industrial processes commonly used to purify IgG from plasma are based on the original method devised by Cohn (Cohn E., et al., (1946), J Am Chem Soc, 68, 459-475, Oncley et al., (1949), J Am Chem Soc, 71, 541-550), which dates back to the 1940s and rely on the cold fractionated precipitation of plasma proteins. After progressive additions of ethanol under controlled conditions of ionic strength, pH and temperature, this plasma fractionation process obtains enriched or concentrated fractions of therapeutically useful plasma proteins (coagulation factors, albumin, immunoglobulin, antithrombin III). Applying Cohn's fractionation, IgG is obtained from fractions II+III, I+II+II or the equivalent precipitate A (called NA precipitate) according Kistler and Nitschmann, who developed a modified ethanol fractionation method (Kistler P and Nitschmann H S, (1952), Vox Sang, 7, 414-424).

In the 1960s it was shown that short fatty acids (C6-C12) form insoluble complexes with $\alpha$- and $\beta$-globulins whereas $\gamma$-globulins are not as readily precipitated (Chanutin et al., (1960) Arch. Biochem. Biophys. 89; 218).

Steinbuch & Audran ((1969) Arch. Biochem. Biophys. 134, 279-294) described a purification process for IgG with caprylate (i.e. octanoate, a C8-saturated fatty acid) as precipitating agent. Non-immunoglobulins were precipitated from human plasma after dilution with an acetate buffer to reach a final pH of 4.8. After addition of caprylate under vigorous stirring an IgG enriched solution was obtained. The purity and yield depended on the amount of caprylic acid, the pH, the molarity of the buffer and the dilution factor.

Extensive non-immunoglobulin precipitation was best obtained at slightly acidic pH, but not below pH 4.5. Plasma was diluted 2:1 with 0.06 M acetate buffer, pH 4.8, and then treated with 2.5 wt. % caprylate to initiate precipitation. Batch adsorption of the supernatant on DEAE-cellulose was used to clear additional impurities from the isolated IgG fraction. Later work by Steinbuch et al. showed the use of caprylic acid to precipitate most proteins and lipoproteins (other than the immunoglobulins) present in Cohn ethanol Fraction III (Steinbuch et al., (1973), Prep. Biochem. 3, 363-373).

The same method was applied to diluted human plasma using 2.16 wt. % caprylate. (Habeeb et al., (1984) Prep. Biochem. 14, 1-17). Habeeb et al. followed the caprylic acid precipitation with fractionation on DEAE cellulose. The resulting plasma-derived IgG was essentially free of aggregates, plasmin and plasminogen. In addition, the IgG obtained was low in anticomplement activity and relatively stable during storage. The caprylate precipitation step was therefore recognized as very useful, and was introduced into many modern processes for IgG production from plasma.

In addition to the alcohol, PEG and caprylic acid fractionation methods, several chromatographic methods were used in combination with basic fractionation methods for the purification of IVIG.

The most commonly used chromatographic method is ion exchange chromatography which takes advantage of surface distribution and charge density on both the protein and the ion exchange media. The anion exchange resin presents a positively charged surface. The charge density is specific to the resin and generally is independent of pH (within the working range of the resin). A typical anion exchanger will bind proteins which have a net negative charge (i.e. when the pH of the solution is above the isoelectric point of the protein). In reality, the surface of a protein does not present a singular charge; rather it is a mosaic of positive and negative charges, and neutral areas. Surface structure is specific to a given protein and will be affected by solution conditions such as ionic strength and pH. This uniqueness can be exploited to establish specific conditions where individual proteins will bind or release from the anion exchange resin. By establishing these conditions, proteins with only slightly differing surface or charge properties can be effectively separated with high yield (>95%).

Improvements in the structure of chromatography resin supports have made large scale chromatography a practical alternative to more conventional purification methods. Rigid resins allow large volumes to be processed rapidly (<5 hours), and high ligand density gives the increased capacity necessary for large volume processing. These factors coupled with high yields, product purity and process simplicity favor the use of chromatography in large scale manufacturing.

In particular, cation and/or anion exchange chromatography, sometimes combined in separate steps or in series, have been used for purifying IgG from plasma or fractions thereof (e.g. as described in WO 99/64462). In the majority of the methods, anion exchange chromatography is used in negative mode, i.e. conditions are used to enable the binding of the contaminant proteins, e.g. IgA, IgM, albumin, fibrinogen, transferrin, while the IgG is recovered in the non-adsorbed fraction.

The combination of caprylate precipitation followed by ion-exchange chromatography for the purification of IgG was described in many publications. Steinbuch & Audran ((1969) Arch Biochem Biophys 134, 279-284) described the further purification of IgG after precipitation of caprylate with DEAE-cellulose. Lebing et al. (U.S. Pat. No. 5,886, 157) described two anion-exchange columns used in series for the removal of IgM, IgA, albumin and other impurities. Lebing et al. combined both caprylate mediated effects, namely the essential reduction of non-IgG proteins by precipitation, thereby using the virus partitioning, and the enveloped virus inactivation properties of the fatty acid in a separate incubation step. The importance of the so-called "pH-swing" starting from the reconstitution of an IgG containing paste/precipitate at pH 4.2 and the subsequent addition of caprylate upon adjusting the pH 5.2 is stressed to be essential for the IgG enriching procedure, thus needed to effectively reduce non-IgG proteins. A few other impurities, like IgA and IgM, as well as the caprylate were subsequently reduced by the mentioned ion exchange chromatography steps.

U.S. Pat. No. 5,164,487 concerns the use of caprylic acid for the manufacture of an intravenously tolerable IgG preparation free from aggregates, vasoactive substances and proteolytic enzymes. The method includes contacting the starting material containing IgG with 0.4% to 1.5% caprylic acid before chromatographic purification with an ion exchange or hydrophobic matrix.

Due to the continuous improvements in purification processes, there has been an evolution in IgG products over the years. As mentioned above, the first IgG products were only suitable for intramuscular use, as they caused too many adverse events when administered intravenously. The first generation of an IgG product suitable for intravenous use (IVIG) was prepared by pepsin cleavage of the starting material (Cohn fraction II), the purpose of the cleavage being removal of immunoglobulin aggregates which caused serious adverse events such as complement activation and made it impossible to administer the early products intravenously. No column chromatography steps were included in the process. The product had to be freeze-dried in order to remain stable for a reasonable period of time and was dissolved immediately prior to use.

A second generation of IVIG based on uncleaved and unmodified immunoglobulin molecules with low anti-complement activity and higher stability was introduced in the mid-eighties, but still in the form of a freeze-dried product. This IVIG was purified by processes including several chromatography steps. Pepsin cleavage was avoided, aggregates and particles were removed by precipitation, and further purification was achieved by column chromatographic ion exchange methods.

For the third generation of IVIG, dedicated virus inactivation steps were included in the processes. While particularly the precipitation steps in the purification processes removed a lot of viruses, some patients treated with blood products nevertheless were infected with HIV, necessitating further, dedicated steps to be taken to inactivate and remove viruses from these products.

The processes were continued to be refined further to achieve better purity and quality of the protein, in order to enable stable liquid products to be made available, and to improve the safety and tolerability of these products for patients. In addition, subcutaneous formulations were developed.

IgG products are now used in a number of clinical applications. In addition to the traditional use for the treatment of primary or acquired immunodeficiencies, and infectious diseases, it has been shown that these products are also effective in the treatment of autoimmune diseases and certain neurological disorders such as CIDP. There has also been a marked increase in the number of studies focusing on further therapeutic uses of IgG products. Thus the demand for IgG products has been increasing. IgG products are now the plasma products in greatest demand on the world market; in 2008 the market reached approximately 82 metric tons (including 37 tons in the USA, 21 tons in Europe and 17 tons in Asia) with a tendency to grow at a rate of approximately 7% a year (the predicted demand in 2013 is 110 metric tons) (The Worldwide Plasma Fractions Market 2008. The Marketing Research Bureau, Inc. April 2010 Edition). As human plasma is a valuable, limited resource, the processes for purification of IgG from plasma need to be further improved to achieve higher yields than currently possible while not compromising the quality of the product. Current processes have an average yield of 3.7 to 4.2 g of IgG per liter of plasma, which represents only up to 55% of the IgG present in plasma.

SUMMARY OF THE INVENTION

The invention relates to a modified process for the purification of IgG from plasma or other solutions comprising IgG and other proteins, improving the yield of IgG per liter of starting solution (preferably plasma) without compromising the quality of the product.

A first aspect of the invention is a method for increasing the yield of IgG in a purification process from a solution comprising IgG, other immunoglobulins and/or other protein contaminants, comprising
(a) providing an acidic solution comprising IgG, other immunoglobulins and/or other protein contaminants with a pH of between 3.5 to 5.2 and a total protein concentration of at least 10 g/l;
(b) adjusting the solution to a pH of 5.2 to 6.2 while maintaining a conductivity of below 1.5 mS/cm;
(c) incubating the solution for at least 15 minutes; and
(d) removing any precipitate.

Preferably, the solution comprising IgG comprises plasma-derived antibodies, more preferably, the solution comprising IgG is obtained by ethanol fractionation of human plasma or human cryo-poor plasma. In another preferred embodiment of the invention, the solution comprising IgG is a supernatant from an octanoic acid precipitation.

Typically, the solution in step (a) has been clarified by ultradiafiltration. Preferably, the pH of the solution in step (a) is 3.9 to 5.0, more preferably 3.9 to 4.6, even more preferably from 3.9 to 4.3. Preferably, the protein concentration in step (a) is between 10 and 50 g/l, more preferably between 20 and 25 g/l.

In step (b), the pH is adjusted to a pH of 5.2 to 6.2, preferably to a pH of 5.6 to 6.0, more preferably to a pH of 5.8 to 6.0. Preferably, the pH adjustment in step (b) is done by addition of at least one multi-hydroxylated amine compound. Preferably, the pH adjustment is done with Tris at a concentration above 250 mM, more preferably above 500 mM, even more preferably above 750 mM, most preferably around 1M. Preferably, the pH adjustment is done over a time period of at least 15 minutes. The conductivity in step (b) is below 1.5 mS/cm, preferably below 1.2 mS/cm, more preferably below 1.0 mS/cm, even more preferably below 0.8 mS/cm, most preferably between 0.2 and 0.5 mS/cm. Most preferably, the pH in step (b) is adjusted to pH 5.6 to 6.0, and the conductivity is between 0.2 and 0.5 mS/cm.

The incubation time in step (c) is up to 72 hours, up to 48 hours, up to 24 hours, preferably up to 12 hours, more preferably up to 6 hours, most preferably between 15 minutes and 90 minutes. Preferably, the incubation in step (c) is carried out at ambient temperature.

The precipitate in step (d) is preferably removed by depth filtration. Other methods for removing the precipitate are also possible, e.g. other filtration methods or centrifugation.

After step (d), further purification steps such as chromatographic methods, e.g. ion exchange chromatography, can be carried out. Preferably, an ion exchange chromatography step is carried out under conditions that allow contaminants but not IgG to bind to the resin. Preferably, the ion exchange chromatography is an anion exchange chromatography. Preferably, the ion exchange chromatography is carried out without further adjustment to the conductivity of the solution.

The method will further comprise a virus inactivation step. Preferably, the virus inactivation step is a low pH treatment. Preferably, the low pH treatment for virus inactivation is carried out prior to step (a).

DETAILED DESCRIPTION OF THE INVENTION

The invention relates to a method for increasing the yield of IgG in a purification process from a starting solution, preferably an intermediate of a current process, comprising IgG antibodies, other immunoglobulins and/or other protein contaminants. The method comprises the steps of:
(a) providing an acidic solution comprising IgG, other immunoglobulins and/or other protein contaminants with a pH of between 3.5 to 5.2, preferably 4.0 to 5.0, more preferably 4.6 to 4.8, and a total protein concentration of at least 10 g/l, preferably about 10 to 50 g/l, more preferably about 10 to 40 g/l, even more preferably 15 to 30 g/l, most preferably 20-25 g/l.

The IgG comprising composition can be any material, preferably it is a biological fluid containing IgG. Preferably, the IgG comprising composition is or is derived from blood, plasma or serum. However, other IgG containing starting materials can also be used in the invention. For example, IgG can also be enriched from other biological fluids such cell culture supernatant using the method of the invention.

The IgG comprising composition may be a solution of a paste or precipitate, preferably a fraction from a cold ethanol fractionation process, such as (FII+III), (F I+II+II) or FIII as described in Cohn/Oncley et. al. or modifications thereof, or precipitate A (PPT-A), precipitate B (PPT-B) and precipitate G (PPT-G) as described in the Kistler and Nitschman process or modifications thereof.

Preferably, however, the IgG comprising solution is a solution of an intermediate precipitate or an intermediate solution obtained during the purification of IgG using octanoic acid-, polyethylene glycol- and/or ammonium sulphate precipitation starting from an ethanol fraction as described above, or any IgG containing intermediate. When starting from plasma fractions, octanoic acid precipitation is a preferred method for producing an intermediate enriched in IgG. Octanoic acid may be added to an intermediate solution, e.g. to a solubilized ethanol precipitate, to a final concentration of around 5% (w/w) as described by Steinbuch & Audran ((1969) Arch. Biochem. Biophys. 134, 279-294). Higher concentrations of octanoic acid may also be used. The octanoic acid should be added slowly, at ambient temperature under defined conditions such pH, conductivity and incubation time. If a higher concentration of octanoic acid is used, calcium phosphate may be added in addition, followed by an additional incubation period. A precipitate of contaminating proteins, lipids and caprylate forms, while the majority of the immunoglobulins, in particular the IgG, remains in solution. Precipitated proteins, lipids, and caprylate may be removed by filtration at ambient temperature (e.g., between 18° C. and 26° C.). For example, depth filtration in the presence of filter aid may be used (for example using diatomaceous earth, but other filter aids may be used). The solution may be filtered using normal flow filtration. However, other methods of removing the precipitate and clarifying the solution are also envisaged. The clarified solution may then be subjected to dia-/ultrafiltration to adjust pH, conductivity, and protein concentration.

Preferably the starting solution is an intermediate solution already enriched with immunoglobulins and clarified by ultra/diafiltration during a process for purification of IgG from plasma or plasma fractions at acidic conditions as described above.

If a precipitate is used as the starting material, the IgG can be extracted from the precipitate (process fraction or side fraction) by resuspending the precipitate in a buffer for several hours. Preferably, the solubilisation is carried out using a solution with a conductivity between 1 and 15 mS/cm, more preferably between 5 and 15 mS/cm. The pH of the solution used for solubilisation is between 3.5 to 6, preferably between 4.0 to 5.5, more preferably between 4.5 to 5.2, most preferably around 4.8. For example, the solubilisation may be carried out with 0.2 M acetate at pH 4.8. However, the skilled person will be able to identify further suitable buffers. The ratio of buffer and precipitate may be about 1:5 to 1:10, but other ratios can also be used. The solubilisation is carried out for at least 2 hours, preferably for at least 4 hours under strong agitation using a suitable mixer.

In the next step of the method of the invention the pH of the solution of step (a) is further adjusted to about 5.2 to 6.2, preferably 5.4 to 6.0, more preferably 5.6 to 6.0, even more preferably 5.7 to 5.9, most preferably around 5.8. The conductivity of this solution independent the pH is below 1.5 mS/cm, e.g. between 0.2 and 1.5 mS/cm, preferably below 1.0 mS/cm, e.g. between 0.2 and 1.0 mS/cm, even more preferably below 0.8 mS/cm, e.g. between 0.2 and 0.8 mS/cm, or even below 0.5 mS/cm, most preferably between 0.2 to 0.5 mS/cm.

Preferably the reagent used to adjust the pH and conductivity is or comprises an amine compound, preferably a multi-hydroxylated amine compound such as 2-Amino-1-ethanol ($C_2H_7NO$), Bis(hydroxyethyl)-amine ($C_4H_{11}NO_2$), Tris(2-hydroxyethyl) amine ($C_6H_{15}NO_3$), preferably (Bis(2-hydroxyethyl)-amino-tris(hydroxymethyl)-methane) ($C_8H_{19}NO_5$), N,N bis(2-hydroxyethyl) glycine ($C_6H_{13}NO_4$), 1,3-bis(tris(hydroxymethyl)methylamino)propane ($C_{11}H_{26}N_2O_6$), most preferably 2-Amino-2-hydroxymethyl-propane-1,3-diol ($C_4H_{11}NO_3$) (Tris base).

The inventor has advantageously found that using a multi-hydroxylated amine compound with or without carboxyl group leads to a low loss of IgG during the second pH adjustment (stabilizing the IgG). The protein contaminants are precipitated, while the conductivity remains constant at the desired value, e.g. 0.2 to 0.5 mS/cm.

In step (c), this IgG-comprising solution is then incubated, under vigorous mixing using a suitable mixer, for at least 15 minutes. The skilled person will be able to adjust the time required for this step, depending on the method used for mixing. The incubation time may be up to 72 h, preferably up to 48 h, more preferably between 12 and 24 h, most preferably between 15 min and 12 h. However, other incubation times may also be used; the skilled person will be aware that for longer incubation times, it may be necessary to use lower temperatures, e.g. 4-8° C., whereas for shorter incubation times, ambient temperature may be chosen.

In step (d), precipitated proteins formed during the pH-shift of step (c) are removed, for example by depth filtration at ambient temperature (e.g., 18-26° C.). The depth filtration requires addition of filter aid, as known to a skilled person. The solution may be filtered using normal flow filtration. However, other methods for removal of precipitated proteins can also be used, e.g. other filtration methods, centrifugation. The skilled person is well aware of other suitable methods for removing precipitates. This step results in significant reduction of IgM and IgA.

The clarified solution may then be processed to purify IgG further. One preferred option is to subject this solution to ion exchange chromatography. Preferably, the solution is loaded onto an anion exchanger under conditions that allow the residual IgA, IgM and other contaminants to bind, while the IgG remains in the flow-through. Preferably, the clarified solution may be directly loaded onto the column. Advantageously, there is no need to adjust pH or conductivity.

The anion exchanger used in this step can be a strong anion exchanger or a week anion exchanger. Preferably, the anion exchanger comprises an anion exchange ligand such as quaternary ammonium, quaternary aminoethyl, diethyl-aminoethyl, trimethylaminoethyl, or dimethylaminoethyl. More preferably, the anion exchanger is selected from DEAE Sepharose FF, Q-Sepharose (HP and FF), ANX Sepharose FF (low and high substituted), Capto Q, Capto Q XP, Capto DEAE, Source 30 Q and 15 Q, most preferably Fractogel DEAE and MPHQ.

As mentioned above, the loading is preferably performed under conditions that allow residual IgA, IgM and other contaminants to bind to the anion exchanger. Typically, the anion exchanger is equilibrated prior to use, often with a two buffer system (equilibration buffer 1 and 2), whereby the equilibration buffer 2 is used prior to loading. The equilibration buffers are a common buffer system adapted to the used anion exchanger. The conductivity of the equilibration buffer 1 is between 10 to 20 mS/cm, more preferably between 11 to 15 mS/cm. The pH is between 7 to 8, more preferably between 7.1 to 7.5. Examples of suitable buffers are Phosphate or acetate buffers or a combination thereof. Preferably, the buffer is a phosphate-mix (mono- and dibasic).

Further steps that may be included in the process are virus inactivation/removal steps such as nanofiltration, solvent/detergent treatment, low pH treatment, or pasteurization. The skilled person will be well aware of suitable virus inactivation and removal methods. These steps can be included at any suitable stage in the process.

Typically, pharmaceutically acceptable excipients such as a stabilizer may be added.

One particularly preferred example of a process where the method of the invention has been successfully implemented is a process comprising cold ethanol fractionation and using either Precipitate A, an intermediate of the base fractionation according to Kistler and Nitschmann, or Precipitate II+III (PPT II+III) obtained according to Cohn et al and/or Precipitate I+II+III obtained according modifications of Kistler-Cohn processes.

The production intermediates are processed essentially by the following steps:
(1) octanoic acid (OA) fractionation,
(2) low pH incubation,
(3) pH-shift and depth filtration,
(4) anion exchange chromatography,
(5) virus filtration, and
(6) concentration by ultra/diafiltration.

Process modification according to the invention comprise one or more of
  (i) pre-purification through changing the pH (pH-shift) prior to the depth filtration. This step is performed at very low conductivity in order to precipitate a great part of IgA and IgM and minimize the co-precipitation of the IgG prior the polishing chromatography step;
  (ii) modifications of the buffer system for the anion exchange chromatography step.

Advantageously, the pH shift is carried out using (preferably) a Tris buffer, which does not increase the conductivity of the solution; the resulting filtrate after depth filtration can thus be loaded directly onto the anion exchange column, which has been appropriately equilibrated, e.g. with a phosphate buffer. The low conductivity is important to reduce the precipitation of IgG in this step.

Using both modifications in the process, the IgG yield increases by at least 5% as compared to the same process without those modifications.

EXAMPLES

The invention will now be exemplified. The examples are intended to illustrate, but not limit the invention. Reference to the following figures is made:

FIG. 1: Bar diagram showing the effect of the pH adjustment in step (b) on protein yield (light grey bars) and IgG yield (black bars).

Figure 2:
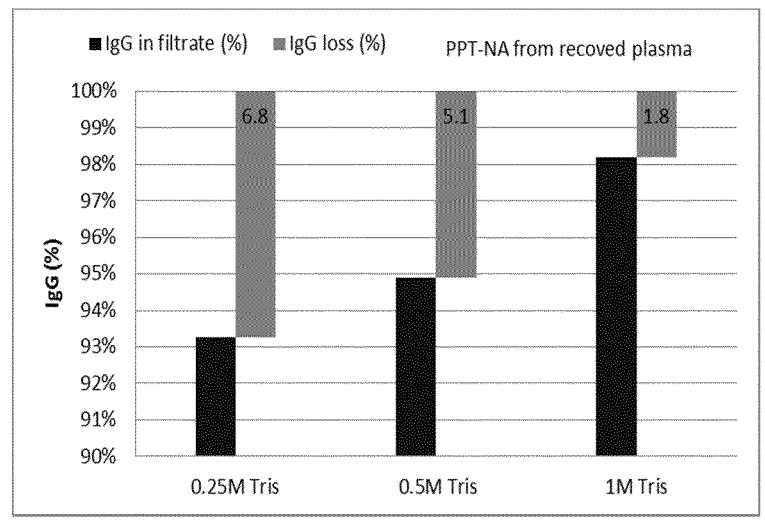
Figure 2:
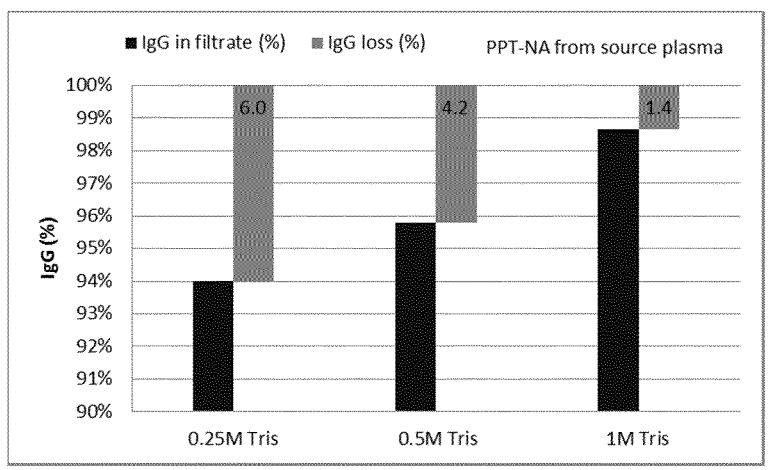
Figure 2:
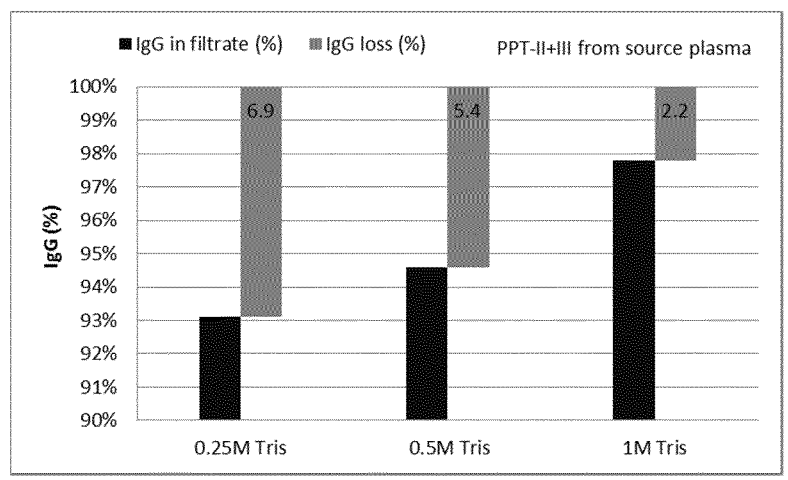

FIG. 2: Bar diagrams showing the effect of the concentration of Tris used for the pH shift to pH5.8 on the IgG yield (black bars) or loss (grey bars) for 3 different starting materials: (a) starting material NA PPT from recovered plasma, (b) starting material NA PPT from source plasma, (c) PPT II+III from source plasma.

EXAMPLE 1

(a) Prior Art Process According to Steinbuch & Audran ((1969) Arch. Biochem. Biophys. 134, 279-294)

One part of frozen NA precipitate (PPT) was re-suspended in an adequate amount of sodium acetate buffer, the NA PPT suspension was stirred for several hours until most of the IgG was dissolved at ambient temperature, while keeping the pH constant at 4.8.

Delipidation was performed by the addition of octanoic acid (OA) to the suspension and a subsequent incubation for 240 minutes. Calcium phosphate was then added and the suspension was stirred for a further 60 to 90 minutes. Precipitated proteins, lipids or lipoprotein complexes and other contaminants precipitated under these conditions were removed by filtration.

The OA-filtrate was subjected to ultrafiltration to reach a protein concentration of 3% followed by diafiltration against Water for Injection (WFI). During diafiltration the pH was continuously shifted towards pH 4.1 with 0.2 mol/L HCl. After diafiltration, the protein solution was diluted with WFI to 20 g/L protein, the pH was adjusted to pH 4.0±0.1 and 23.5 mg/kg polysorbate 80 (P80) was added. After filtration and a post-filtration wash, a pH 4.0 incubation was performed at 37° C. for several hours at a protein concentration of about 20 g/L. The pH 4-incubated material was then cooled to RT.

The pH was increased to pH 6.5 with NaOH followed by incubation for about 90 min. The pH adjustment and incubation removed a significant part of the IgA and IgM by precipitation. The precipitated impurities were removed by filtration. After adjustment of the conductivity, the clear solution was filtered inline and applied to a column, which was conditioned and equilibrated with 10 mM sodium-acetate, pH 6.5, filled with a strong anion exchanger (Macroprep High Performance; MPHQ). Under the given conditions residual IgA and IgM as well as other protein impurities bound to the anion exchange (AIEX) resin, while IgG was found in the flow through and wash fractions. During collection, the pH of the AIEX flow through and wash containing IgG was lowered to and maintained at pH 4.8±0.1.

Virus removal was achieved by a 0.1 μm pre-filtration followed by nanofiltration inline. The virus filtrate was concentrated to 2-3% protein, using a Polyethersulfon membrane, and diafiltered against WFI. During the diafiltration the pH was continually shifted towards pH 4.1. Afterwards the solution was concentrated to a protein content of 105-135 g/L. The drug substance was diluted to 100 g IgG per liter, stabilised with 250 mmol/L L-Proline (final concentration) and the pH was maintained at 4.80±0.10. The formulated bulk was particle filtered through a 0.2 μm membrane filter.

(b) Modified Process Including pH Shift and Optimization of the Chromatography Buffer System The process as described in (a) was modified by the implementation of the pH-shift step and optimization of the buffer system for the chromatography according to this invention.

The NA PPT was processed as described above, including OA precipitation and low pH virus inactivation.

The pH of the low pH 4 incubated solution was then adjusted to pH 5.8 using 1M Tris buffer. The pH adjustment was carried out over a time period of 90 min, followed by incubation for 90 min at ambient temperature. The precipitate formed was then removed by filtration. The pH and conductivity remained constant as described in step (b) of claim 1, e.g. at a pH of around 5.8 and conductivity around 0.2-0.5 mS/cm.

After conditioning, using a phosphate buffer (0.12 M phosphate, pH 7.3±0.2), and equilibration, using (5 mM Phosphat+10 mM Acetate, pH 6.0±0.1), the chromatography column filled with a strong anion exchanger (Macroprep High Performance; MPHQ) was loaded with ≤180 g protein per Liter of resin at a linear flow of 70-130 cm/h. Under the given conditions residual IgA and IgM as well as other protein impurities bound to the anion exchange (AIEX) resin, while IgG was found in the flow through and wash fractions. During collection, the pH of the AIEX flow through and wash containing IgG was lowered to and maintained at pH 4.8±0.1.

The following steps were carried out as described in (a). Yield Comparison (Current Vs. Modified Process)

The comparison of the two processes with respect to the protein yield from the same starting intermediate is shown in Tables 1 to 3. The IgG yield after the low pH incubation (pH 4) was set as 100%.

TABLE 1

Comparison between prior art and modified process - Starting material NA generated from recovered plasma

| Step | Prior art process | Modified process |
|---|---|---|
| Plasma equivalent (L) Post low pH incubation | 11195 | 239.6 |
| Protein Yield (%) Post pH-shift and filtration | 100 | 100 |
| Protein Yield (%) Post chromatography | 90.7 | 94.5 |
| Protein Yield (%) Post bulk formulation | 78 | 84 |
| Protein Yield (%) | 77.6 | 83.3 |

TABLE 2

Comparison between prior art and modified process - Starting material NA generated from source plasma

| Step | Prior art process | Modified process |
|---|---|---|
| Plasma equivalent (L) Post low pH incubation | 13196 | 300.66 |
| Protein Yield (%) Post pH-shift and filtration | 100 | 100 |
| Protein Yield (%) Post chromatography | 91 | 96 |
| Protein Yield (%) Post bulk formulation | 78 | 84 |
| Protein Yield (%) | 77 | 83 |

TABLE 3

Comparison between prior art and modified process - Starting material PPTII + III generated from source plasma

| Step | Current process | Modified process |
|---|---|---|
| Plasma equivalent (L) Post low pH incubation | 13494 | 304.2 |
| Protein Yield (%) Post pH-shift and filtration | 100 | 100 |
| Protein Yield (%) Post chromatography | 96 | 100 |
| Protein Yield (%) Post bulk formulation | 80 | 85 |
| Protein Yield (%) | 79 | 84 |

It was shown that no significant changes in the purity of the product occurred as a result of the changes in the process and increased yields.

EXAMPLE 2

This example demonstrates the impact of different pH-adjustments using Tris buffer on IgG yield compared to the current pH-shift of 6.5.

Starting from PPT-NA as described in Example 1, a low pH 4 incubated solution was generated as described above. Eight portions of 1 kg each were taken and adjusted to pH of 5.2; 5.4; 5.6; 5.8; 6.0; 6.2; 6.4 using 1M Tris buffer. The pH of the last portion was adjusted using 0.2M NaOH according to the current process. The pH adjustment was carried out over a time period of 90 min. followed by incubation of 90 min at ambient temperature as described above. The precipitate formed was then removed by filtration. The filtrate was then loaded onto the AIEX column as described in Example 1(b). The protein and IgG-yield of the different loaded solutions were compared. The results are shown in FIG. 1. The impact of 1M Tris buffer at different pH-shifts compared to the 0.2M NaOH as used for the prior art process as described in Example 1(a), on the IgG yield, indicate that with increasing pH-shift (pH: 5.2-6.2) using 1M Tris buffer, the loss of IgG yield is minimized.

EXAMPLE 3

This example shows the impact of the concentration of the Tris buffer used at the desired pH-shift to 5.8. Starting from the low pH 4 incubated solution, the pH was shifted from pH 4 to 5.8 using 1M; 0.5M and 0.25M Tris buffer respectively.

The results are shown in FIG. 2. Independent from the starting material (source PPT-II+III, NA, or recovered NA), the IgG loss decreased with the increased molarity of the Tris buffer used.

EXAMPLE 4

This example demonstrates the impact of different reagents (comprising an amine compound, preferably a multi-hydroxylated amine compound) used to adjust the pH in step (b), on IgG yield.

The following reagents were used: 2-Amino-1-ethanol (C2H7NO), Bis(hydroxyethyl)-amine (C4H11NO2), Tris(2-hydroxyethyl) amine (C6H15NO3), preferably Bis(2-hydroxyethyl)-amino-tris(hydroxymethyl)-methane (C8H19NO5), N,N bis(2-hydroxyethyl) glycine (C6H13NO4), 1,3-bis(tris(hydroxymethyl)methylamino) propane (C11H26N2O6), 2-Amino-2-hydroxymethyl-propane-1,3-diol (C4H11NO3) (Tris base), as well as combinations of these reagents.

Starting from PPT-NA as described in Example 1, a low pH 4 incubated solution was generated as described above. Eight portions of 1 kg each were taken and adjusted to pH of 5.75 to 5.85 using 1M solutions of the reagents described above. The pH of the last portion was adjusted using 0.2M NaOH according to the current process. The pH adjustment was carried out over a time period of 90 min, followed by incubation of 90 min at ambient temperature as described above. The precipitate formed was then removed by filtration. The IgG-yields of the different filtrates were compared.

The results are shown in Table 4. The results show the impact of using the different reagents (as 1M solutions) for the pH-shift in step (b), as compared to using 0.2M NaOH as used in the prior art process, on the IgG yield. The results indicate that with different amine compounds the IgG yield is increased as compared to the prior art process. Particularly advantageous is the use of multi-hydroxylated amine compounds.

TABLE 4

Comparison between prior art and modified process using different neutralization reagents in comparison to the prior art process - Starting material NA generated from source plasma

| Step | Prior art process IgG Yield (%) | Modified process IgG Yield (%) |
| --- | --- | --- |
| Post low pH incubation | 100 | 100 |
| Post pH-shift and filtration using | | |
| 0.2M NaOH | 91 | — |
| Tris | — | 95.5 |
| Monoethanol amine | — | 94.1 |
| Diethanolamine | — | 95 |
| Triethanol amine | — | 92.8 |
| Bis tris methan | — | 95.2 |
| Bis tris propane | — | 92.5 |
| N,N bis(2-hydroxyethyl) glycine + Monoethanol amine | — | 98.8 |

The invention claimed is:

1. A method for increasing the yield of IgG in a purification process from a solution comprising IgG and further comprising other immunoglobulins, and/or other protein contaminants, said method comprising
   (a) providing an acidic solution comprising IgG and further comprising other immunoglobulins, and/or other protein contaminants, said solution having a pH of between 3.5 to 5.2 and a total protein concentration of at least 10 g/l;
   (b) adjusting the solution to a pH of 5.2 to 6.2 while maintaining a conductivity of below 1.5 mS/cm;
   (c) incubating the solution for at least 15 minutes; and
   (d) removing any precipitate.

2. The method of claim 1, wherein the solution comprising IgG comprises plasma-derived antibodies.

3. The method of claim 1, wherein the solution comprising IgG is obtained by ethanol fractionation of human plasma or human cryo-poor plasma.

4. The method of claim 3, wherein the solution comprising IgG is a supernatant from an octanoic acid precipitation.

5. The method of claim 1, wherein the solution in step (a) has been clarified by ultradiafiltration.

6. The method of claim 1, wherein the pH of the solution in step (a) is 3.9 to 5.0, 3.9 to 4.6, or 3.9 to 4.3.

7. The method of claim 1, wherein the protein concentration in step (a) is between 10 and 50 g/l or between 20 and 25 g/l.

8. The method of claim 1, wherein the pH in step (b) is adjusted to pH 5.6 to 6.0 or pH 5.8 to 6.0.

9. The method of claim 1, wherein the pH adjustment in step (b) is done by addition of at least one multi-hydroxylated amine compound with or without a carboxyl group.

10. The method of claim 1, wherein the conductivity in step (b) is adjusted with Tris at a concentration above 250 mM, at a concentration above 500 mM, at a concentration above 750 mM, or at a concentration around 1M.

11. The method of claim 1, wherein the conductivity in step (b) is below 1.0 mS/cm, below 0.8 mS/cm, or between 0.2 and 0.5 mS/cm.

12. The method of claim 1, wherein the pH in step (b) is adjusted to pH 5.6 to 6.0 and the conductivity is between 0.2 and 0.5 mS/cm.

13. The method of claim 1, wherein the incubation time in step (c) is up to 72 hours, up to 48 hours, up to 24 hours, up to 12 hours, up to 6 hours, or between 15 minutes and 90 minutes.

14. The method of claim 1, wherein the incubation in step (c) is carried out at ambient temperature.

15. The method of claim 1, wherein the precipitate in step (d) is removed by depth filtration.

16. The method of claim 1, wherein after step (d), an ion exchange chromatography step is carried out under conditions that allow contaminants but not IgG to bind to the resin.

17. The method of claim 16, wherein the ion exchange chromatography is an anion exchange chromatography.

18. The method of claim 16, wherein the ion exchange chromatography is carried out without further adjustment to the conductivity of the solution.

19. The method of claim 1, further comprising a virus inactivation step.

20. The method of claim 19, wherein the virus inactivation step is a low pH treatment.

21. The method of claim 20 wherein the low pH treatment is carried out prior to step (a).

\* \* \* \* \*